(12) United States Patent
Marsh et al.

(10) Patent No.: US 10,330,541 B2
(45) Date of Patent: Jun. 25, 2019

(54) NANOCOMPOSITE OPTICAL STRAIN GAUGE

(71) Applicants: Charles P Marsh, Urbana, IL (US); Kyle B Ford, Urbana, IL (US); Nassim E Ajami, Downers Grove, IL (US); Michael Collins, Orland Park, IL (US)

(72) Inventors: Charles P Marsh, Urbana, IL (US); Kyle B Ford, Urbana, IL (US); Nassim E Ajami, Downers Grove, IL (US); Michael Collins, Orland Park, IL (US)

(73) Assignee: THE UNITED STATES OF AMERICA AS REPRESENTED BY THE SECRETARY OF THE ARMY, Washington, DC (US)

(*) Notice: Subject to any disclaimer, the term of this patent is extended or adjusted under 35 U.S.C. 154(b) by 0 days.

(21) Appl. No.: 14/725,365

(22) Filed: May 29, 2015

(65) Prior Publication Data
US 2017/0074732 A1 Mar. 16, 2017

(51) Int. Cl.
G01L 1/24 (2006.01)
G01N 21/64 (2006.01)

(52) U.S. Cl.
CPC .............. *G01L 1/24* (2013.01); *G01N 21/645* (2013.01); *G01N 2021/6417* (2013.01); *G01N 2201/06113* (2013.01); *G01N 2201/127* (2013.01)

(58) Field of Classification Search
None
See application file for complete search history.

(56) References Cited

PUBLICATIONS

Shilpa N. Raja et al. "Tetrapod Nanocrystals as Fluorescent Stress Probes of Electrospun Nanocomposites" Nano Lett. 13, 3915-3922 (2013).*
Roithner LaserTechnik "Roithner 532" (datasheet) (2014).*
S.A. Wade et al., "Fluorescence intensity ratio technique for optical fiber point temperature sensing" J. Appl. Phys., vol. 94, No. 8, (2003).*
Giita Silverajah et al., "A Comparative Study on the Mechanical, Thermal and Morphological Characterization of Poly(lactic acid)/ Epoxidized Palm Oil Blend", Int J Mol Sci. 13(5): 5878-5898 (2012).*

* cited by examiner

*Primary Examiner* — Edwin Gunberg
(74) *Attorney, Agent, or Firm* — Brian C. Jones

(57) ABSTRACT

The pressure-detecting system utilizes a nanocomposite sensor with quantum dots embedded in a matrix. Under pressure, both the quantum dots and the matrix fluoresce when illuminated by a laser. A spectroscope detects the intensity of each fluorescence and sends the information to a data processor. The data processor calculates a ratio using the intensities. Comparing this ratio to ratios stored in a data object in a database provides a value for the pressure detected by the sensor. The data object contains multiple ratios, each correlated to a specific pressure during a calibration process for the sensor. This calibration process subjected the sensor to known pressures, with the resultant ratios calculated and stored in the data object, correlated to the appropriate pressures.

20 Claims, 4 Drawing Sheets

NANOCOMPOSITE OPTICAL STRAIN GAUGE

STATEMENT OF GOVERNMENT INTEREST

The invention described herein was made by an employee of the United States Government and may be manufactured and used by the Government of the United States of America for governmental purposes without the payment of any royalties thereon or therefore.

BACKGROUND

1. Field of Invention

This invention relates to the field of nanotechnology, and more specifically to a nanoparticle exhibiting three-dimensional carrier confinement within a specified matrix material.

2. Description of the Related Art

Many material science and civil engineering applications require measurement of localized pressure loading to a high degree of spatial resolution, as well the study the response of large or complex systems, such as structures, to pressure loads. Localized material responses are associated with high pressure from shocks, high explosives, gas-gun and laser-driven events at high spatial resolution. For example, the high energy density of pulsed lasers in laser fusion can be used to compress matter to high densities and temperatures, and subsequently produce high pressure loading in solids.

It is a problem in that art that traditional pressure sensors, such as bonded resistance strain gauges are impractical for taking measurements at necessary locations. Sensors known in the art require extensive wiring and instrumentation. The complexity of wiring and instrumentation increases with the size of the system measured and cannot be quickly deployed. For example, sensors known in the art are impractical for taking measurements from locations that may be difficult to access, such as the upper exterior surfaces of skyscrapers or the undersides of river bridges. In addition, the scale of traditional pressure sensors reduces possible pressure mapping resolution.

Some sensors known in the art utilize the fluorescence of carbon nanotubes and quantum dots. These sensors rely on measurement of wavelength shift in carbon nanotubes or measurement of quantum dot fluorescence. However, these values are only measurable when the sensors are subjected to pressures on the order of gigapascals (GPa). The sensitivity of these sensors is inadequate to measure pressures on the order of megapascals (MPa) or lower.

There is an unmet need in the art for a sensor capable of being deployed to dangerous or inaccessible locations and which can be used to probe a localized material response to pressure at high spatial resolution.

There is a further unmet need in the art for a readily deployable sensor capable of measuring pressures on the order of MPa.

SUMMARY OF THE INVENTION

In one embodiment of the invention, a pressure sensing system includes a laser light source, at least one nanocomposite pressure sensor and a spectrometer and a database operatively coupled to a data processor. The laser light source transmits light in the visible spectrum. The at least one nanocomposite pressure sensor includes a plurality of quantum dots embedded in a sensor matrix. The database includes at least one data object, which includes an array to store a plurality of pressure values P and a plurality of fluorescence intensity ratio $R_F$.

Another embodiment of the invention is a method for using a nanocomposite pressure sensor including a plurality of quantum dots embedded in a sensor matrix. The method illuminates the nanocomposite pressure sensor with a laser light source transmitting light in the visible spectrum. Next, the method detects a returned quantum dot intensity of a quantum dot fluorescence using a spectrometer operatively coupled to a data processor. The method then detects a returned sensor matrix intensity of a sensor matrix fluorescence using the spectrometer. Next, the method converts the returned quantum dot intensity and the returned sensor matrix intensity to a digital format using the spectrometer. The method then transmits the returned quantum dot intensity and the returned sensor matrix intensity to the data processor. Next, the method calculates an actual fluorescence intensity ratio $R_{FA}$ from the returned quantum dot intensity and the returned sensor intensity. The method then compares the actual fluorescence intensity ratio $R_{FA}$ with fluorescence intensity ratios $R_F$ from a database operatively coupled to the data processor and including at least one data object including an array storing a plurality of pressure values P and a plurality of fluorescence intensity ratio $R_F$. Next, the method outputs a pressure value P correlated to one of the plurality of fluorescence intensity ratios $R_F$.

Another embodiment of the invention is a method for calibrating a nanocomposite pressure sensor including a plurality of quantum dots embedded in a sensor matrix. The method instantiates a data object for the nanocomposite pressure sensor. The data object includes an array to store a plurality of pressure values P and a plurality of fluorescence intensity ratio $R_F$. The method then iteratively invokes a function including the following steps n times. The function places the nanocomposite pressure sensor under a known load having a pressure value P. Next, the function illuminates the nanocomposite pressure sensor with a laser light source transmitting light in the visible spectrum. The function then detects a returned quantum dot intensity of a quantum dot fluorescence using a spectrometer operatively coupled to a data processor. Next, the function detects a returned sensor matrix intensity of a sensor matrix fluorescence using the spectrometer. The function then converts the returned quantum dot intensity and the returned sensor matrix intensity to a digital format using the spectrometer. Next, the function transmits the returned quantum dot intensity and the returned sensor matrix intensity to the data processor. The function then calculates a fluorescence intensity ratio $R_F$ using the returned quantum dot intensity and the returned sensor intensity. Next, the function updates the data object with the fluorescence intensity ratio $R_F$ and the pressure value P.

TERMS OF ART

As used herein, the term "solid shape" means the configuration of a discrete three-dimensional solid.

As used herein, the term "visible spectrum" means the portion of the electromagnetic spectrum detectable by the human eye, ranging in wavelength from approximately 390 nm to approximately 700 nm.

DETAILED DESCRIPTION OF INVENTION

Figure 1:
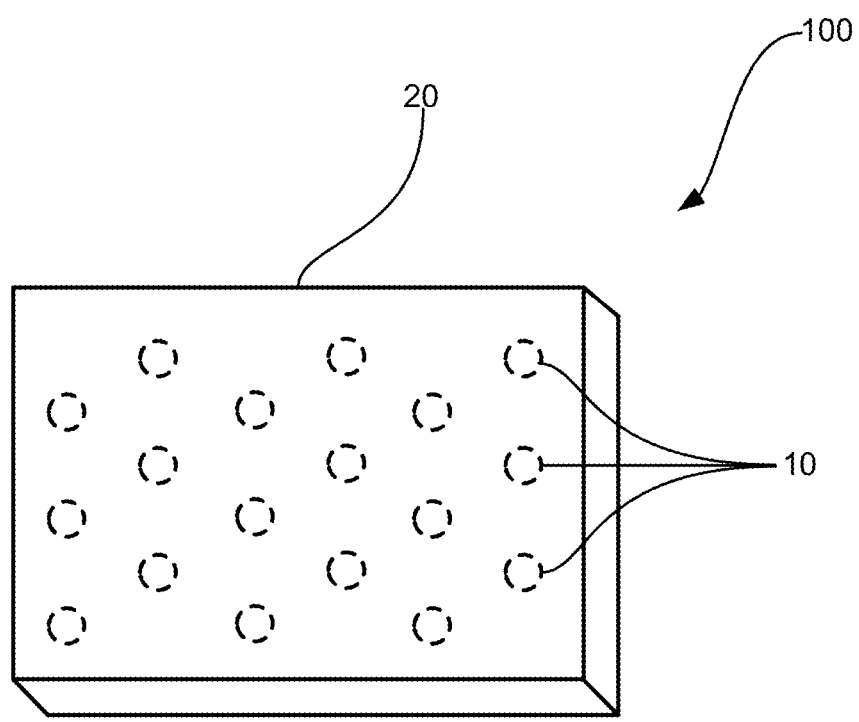
FIG. 1 illustrates an exemplary embodiment of a nanocomposite pressure sensor.

FIG. 1 illustrates an exemplary embodiment of a nanocomposite pressure sensor 100. Nanocomposite pressure sensor 100 includes a plurality of quantum dots 10 embedded in a sensor matrix 20. In the exemplary embodiment, nanocomposite pressure sensor 100 may take the form of a cuboid solid shape. In other embodiments, solid shapes may include, but are not limited to, a prism, a cube, a cylinder, a pyramid, a cone, a disk, a sphere or any combination thereof. In another embodiment, nanocomposite pressure sensor 100 takes the form of a coating on an object.

In the exemplary embodiment, quantum dots 10 are core-shell semiconducting nanocrystals. In one embodiment, quantum dots 10 are CdSe/ZnS core-shell quantum dots functionalized with mercaptoundecanoic acid. Quantum dots 10 fluoresce when subjected to tension or compression pressure loading in the range of approximately 0.5 MPa to approximately 110 MPa. In various embodiments, quantum dots 10 have a diameter of approximately 1 nm to approximately 10 nm, with a maximum diameter variation of approximately 4 nm between quantum dots 10.

Sensor matrix 20 is a polymer having a transmittance of approximately 95% to approximately 100% for the visible spectrum. Sensor matrix 20 also changes intensity of fluorescence when subjected to tension or compression loading in the range of approximately 0.5 MPa to approximately 110 MPa. Under pressure, the intensity of fluorescence of sensor matrix 20 serves as a comparative baseline for the intensity of fluorescence of quantum dots 10. In the exemplary embodiment, sensor matrix 20 is a substantially transparent epoxy such as, but not limited to, Epo-tek® 305, Epo-tek® 301-L and Crystal Clear® 200 epoxy.

Figure 2:
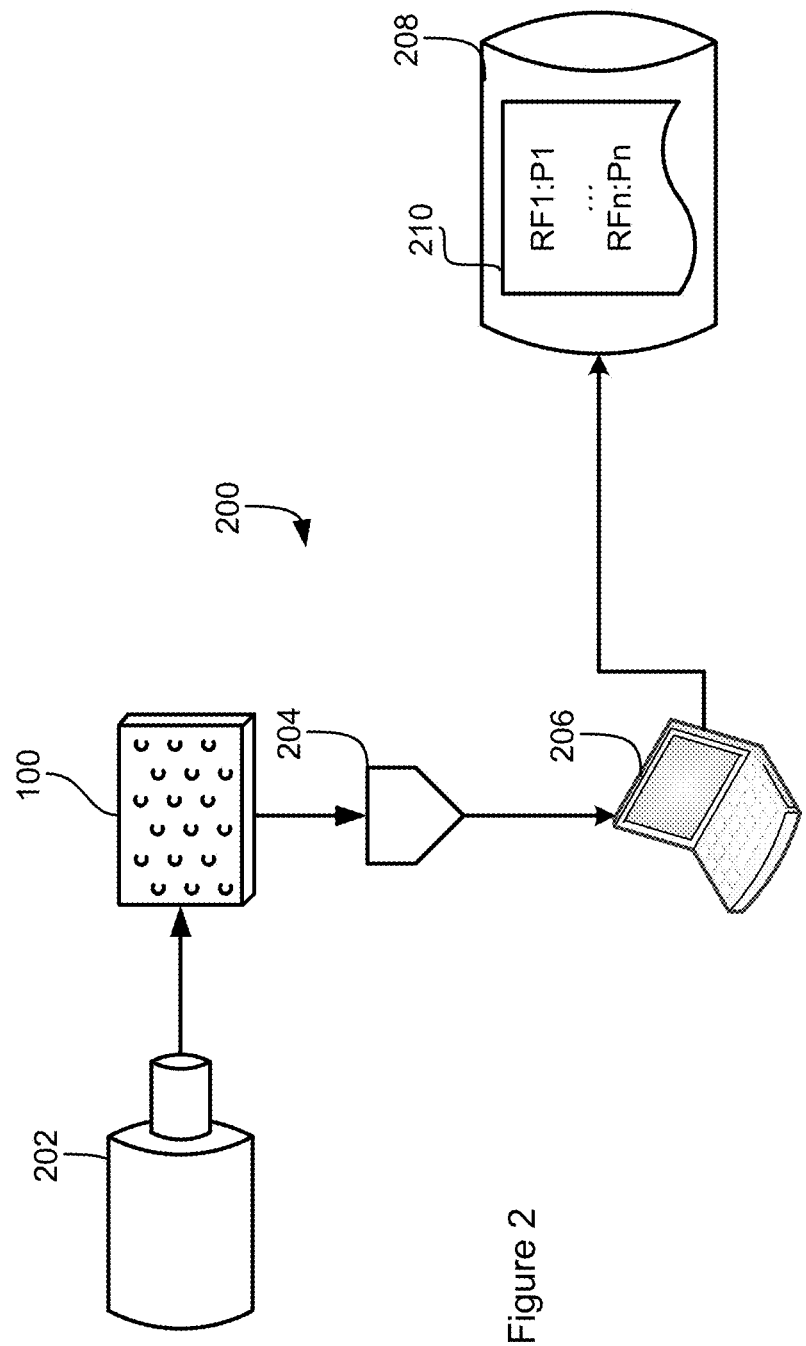
FIG. 2 illustrates an exemplary embodiment of an optical pressure sensing system.

FIG. 2 illustrates an exemplary embodiment of an optical pressure sensing system 200. Optical pressure sensing system 200 includes at least one nanocomposite pressure sensor 100, a laser light source 202, a spectrometer 204, a data processor 206 and a database 208.

Laser light source 202 transmits light in the visible spectrum. In the exemplary embodiment, laser light source 202 is a solid-state source with a power level of 5 mW. Laser light source 202 has a low variation in intensity, having a maximum intensity variation of approximately 1.5%.

Under pressure, quantum dots 10 and sensor matrix 20 of nanocomposite pressure sensor 100 fluoresce when illuminated by laser light. Spectrometer 204 detects the intensity of these resultant light emissions and converts the detected data to a digital format for transmission to data processor 206. In one embodiment, spectrometer 204 is a widespectrum spectrometer. In another embodiment, spectrometer 204 is an optical bandpass detector.

Data processor 206 is operatively coupled to spectrometer 204 to receive fluorescence data from quantum dots 10 and sensor matrix 20. Because applied pressure causes a change in fluorescence intensity for both quantum dots 10 and sensor matrix 20, data processor 206 is configured to calculate the ratio of the fluorescence intensity of quantum dots 10 to the fluorescence intensity of sensor matrix 20. Data processor 206 then utilizes the fluorescence intensity ratio $R_F$ to determine pressure by comparing the fluorescence intensity ratio $R_F$ to fluorescence intensity ratios $R_F$ found in database 208. In one embodiment, data processor 206 instantiates a data object 210 having an array of pressure values P and fluorescence intensity ratios $R_F$.

Database 208 includes at least one data object 210 having an array of pressure values P and fluorescence intensity ratios $R_F$. This data object 210 is quasi-unique to the combination of quantum dots 10 and sensor matrix 20 in nanocomposite pressure sensor 100. As a result, database 208 may contain different data objects 210 for different nanocomposite pressure sensors 100. Database 208 is operatively connected to data processor 206.

Figure 3:
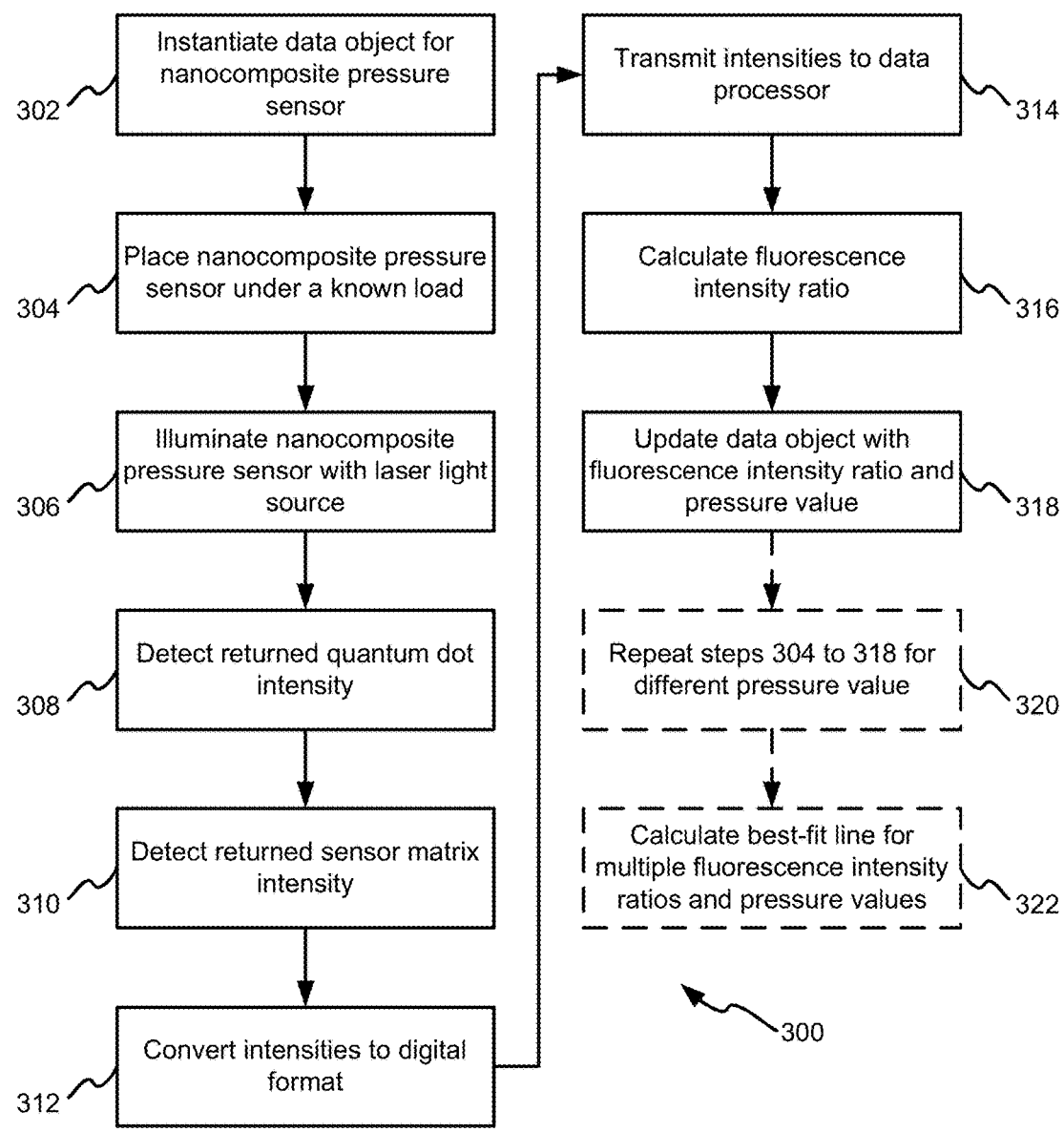
FIG. 3 illustrates a flowchart of an exemplary method for calibrating a nanocomposite pressure sensor.

FIG. 3 illustrates a flowchart of an exemplary method 300 for calibrating nanocomposite pressure sensor 100.

In step 302, method 300 instantiates data object 210 for nanocomposite pressure sensor 100. Data object 210 includes an array to store a plurality of pressure values P and a plurality of fluorescence intensity ratio $R_F$.

In step 304, method 300 places nanocomposite pressure sensor 100 under a known load with a pressure value P. Pressure value P ranges from approximately 0.5 MPa to approximately 110 MPa.

In step 306, method 300 illuminates nanocomposite pressure sensor 100 under pressure with laser light source 202, causing fluorescence in quantum dots 10 and sensor matrix 20.

In step 308, method 300 detects the returned quantum dot intensity of the resulting fluorescence of quantum dots 10 using spectrometer 204.

In step 310, method 300 detects the returned sensor matrix intensity of the resulting fluorescence of sensor matrix 20 using spectrometer 204.

In step 312, method 300 converts the returned quantum dot and sensor matrix intensities to a digital format using spectrometer 204.

In step 314, method 300 transmits the returned quantum dot and sensor matrix intensities to data processor 206.

In step 316, method 300 calculates the fluorescence intensity ratio $R_F$ from the returned quantum dot and sensor matrix intensities using data processor 206.

In step 318, method 300 updates data object 210 with fluorescence intensity ratio $R_F$ and pressure value P.

In optional step 320, method 300 repeats steps 304 to 318 for a different pressure value P.

In optional step 322, method 300 calculates a best-fit line for a plurality of fluorescence intensity ratios $R_F$ and pressure values P. In certain embodiments, this line is calculated using a model such as, but not limited to, hybrid Voigt, Gaussian or Lorentz distribution.

Figure 4:
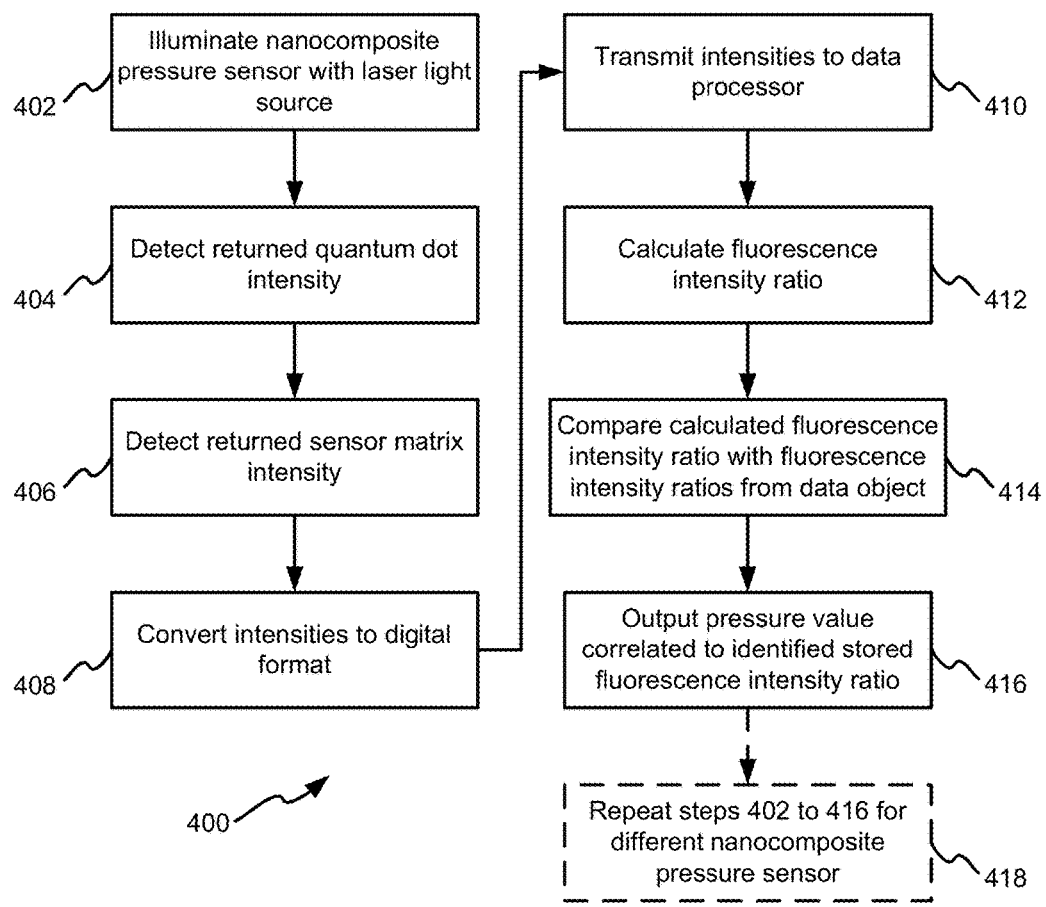
FIG. 4 illustrates a flowchart of an exemplary method for detecting pressure using an optical pressure sensing system.

FIG. 4 illustrates a flowchart of an exemplary method 400 for detecting pressure using an optical pressure sensing system 200.

In step 402, method 400 illuminates nanocomposite pressure sensor 100 with laser light source 202, causing fluorescence in quantum dots 10 and sensor matrix 20.

In step 404, method 400 detects the returned quantum dot intensity of the resulting fluorescence of quantum dots 10 using spectrometer 204.

In step 406, method 400 detects the returned sensor matrix intensity of the resulting fluorescence of sensor matrix 20 using spectrometer 204.

In step 408, method 400 converts the returned quantum dot and sensor matrix intensities to a digital format using spectrometer 204.

In step 410, method 400 transmits the returned quantum dot and sensor matrix intensities to data processor 206.

In step 412, method 400 calculates an actual fluorescence intensity ratio $R_{FA}$ from the returned quantum dot and sensor matrix intensities using data processor 206.

In step 414, method 400 compares the calculated fluorescence intensity ratio $R_F$ with values for fluorescence intensity ratios $R_F$ from data object 210 using data processor 206.

In step 416, method 400 outputs the pressure value P correlated to the identified closest stored fluorescence intensity ratio $R_F$ using data processor 206.

In optional step 418, method 400 repeats steps 402 to 416 for a different nanocomposite pressure sensor 100.

It will be understood that many additional changes in the details, materials, procedures and arrangement of parts, which have been herein described and illustrated to explain the nature of the invention, may be made by those skilled in the art within the principle and scope of the invention as expressed in the appended claims.

It should be further understood that the drawings are not necessarily to scale; instead, emphasis has been placed upon illustrating the principles of the invention. Moreover, the terms "substantially" and "approximately" as used herein may be applied to modify any quantitative representation that could permissibly vary without resulting in a change in the basic function to which it is related.

What is claimed is:

1. A pressure sensing system, comprising: a laser light source, wherein said laser light source transmits light in the visible spectrum; at least one nanocomposite pressure sensor, wherein said at least one nanocomposite pressure sensor comprises a plurality of quantum dots embedded in a sensor matrix, wherein under pressure, said quantum dots and said sensor matrix fluoresce when illuminated by said laser; a spectrometer operatively coupled to a data processor; a database operatively coupled to said data processor, said database comprising at least one data object, wherein said data object comprises an array to store a plurality of pressure values P and a plurality of fluorescence intensity ratio $R_F$.

2. The system of claim 1, wherein said laser light source is a solid-state laser having a power of 5 mW.

3. The system of claim 1, wherein said at least one pressure sensor is a solid shape.

4. The system of claim 1, wherein said at least one pressure sensor is a coating on an object.

5. The system of claim 1, wherein said plurality of quantum dots are core-shell semiconducting nanocrystals.

6. The system of claim 5, wherein said plurality of quantum dots are CdSe/ZnS core-shell quantum dots.

7. The system of claim 1, wherein said plurality of quantum dots have a diameter of approximately 1 nm to approximately 10 nm.

8. The system of claim 1, wherein said plurality of quantum dots have a maximum diameter variation of approximately 4 nm.

9. The system of claim 1, wherein said sensor matrix is a polymer having a transmittance of approximately 95% to approximately 100% for the visible spectrum.

10. The system of claim 9, wherein said sensor matrix is an epoxy.

11. The system of claim 1, wherein said spectrometer is an optical bandpass detector.

12. The system of claim 1, wherein said sensor matrix changes in intensity of fluorescence when subjected to tension or compression loading in the range of approximately 0.5 MPa to approximately 110 MPa, and wherein said intensity of fluorescence of the sensor matrix serves as a comparative baseline for an intensity of fluorescence of the plurality of quantum dots.

13. A method for sensing pressure using a nanocomposite pressure sensor, comprising the steps of: illuminating said nanocomposite pressure sensor with a laser light source, wherein said nanocomposite pressure sensor comprises a plurality of quantum dots embedded in a sensor matrix, wherein said laser light source transmits light in the visible spectrum; wherein under pressure, said quantum dots and said sensor matrix fluoresce when illuminated by said laser; detecting a returned quantum dot intensity of a quantum dot fluorescence using a spectrometer operatively coupled to a data processor; detecting a returned sensor matrix intensity of a sensor matrix fluorescence using said spectrometer; converting said returned quantum dot intensity and said returned sensor matrix intensity to a digital format using said spectrometer; transmitting said returned quantum dot intensity and said returned sensor matrix intensity to said data processor; calculating an actual fluorescence intensity ratio $R_{FA}$ from said returned quantum dot intensity and said returned sensor intensity; comparing said actual fluorescence intensity ratio $R_{FA}$ with fluorescence intensity ratios $R_F$ from a database operatively coupled to said data processor, said database comprising at least one data object, wherein said data object comprises an array storing a plurality of pressure values P and a plurality of fluorescence intensity ratio $R_F$; and outputting a pressure value P correlated to one of said plurality of fluorescence intensity ratios $R_F$.

14. The method of claim 13, further comprising the step of repeating said method using a different nanocomposite pressure sensor.

15. The method of claim 13, wherein said sensor matrix changes in intensity of fluorescence when subjected to tension or compression loading in the range of approximately 0.5 MPa to approximately 110 MPa, and wherein said intensity of fluorescence of the sensor matrix serves as a comparative baseline for an intensity of fluorescence of the plurality of quantum dots.

16. A method for calibrating a nanocomposite pressure sensor, comprising the steps of: instantiating a data object for said nanocomposite pressure sensor, wherein said data object comprises an array to store a plurality of pressure values P and a plurality of fluorescence intensity ratio R.sub.F, wherein said nanocomposite pressure sensor comprises a plurality of quantum dots embedded in a sensor matrix and wherein under pressure, said quantum dots and said sensor matrix fluoresce when illuminated by said laser; and iteratively invoking a function n times, wherein said function comprises the steps of: placing said nanocomposite pressure sensor under a known load, wherein said known load has a pressure value P; illuminating said nanocomposite pressure sensor with a laser light source, wherein said laser light source transmits light in the visible spectrum; detecting a returned quantum dot intensity of a quantum dot fluorescence using a spectrometer operatively coupled to a data processor; detecting a returned sensor matrix intensity of a sensor matrix fluorescence using said spectrometer; converting said returned quantum dot intensity and said returned sensor matrix intensity to a digital format using said spectrometer; transmitting said returned quantum dot intensity and said returned sensor matrix intensity to said data processor; calculating a fluorescence intensity ratio $R_F$ using said returned quantum dot intensity and said returned sensor intensity; and updating said data object with said fluorescence intensity ratio $R_F$ and said pressure value P.

17. The method of claim 16, further comprising the step of repeating said function using a different pressure value P.

18. The method of claim 16, further comprising the step of calculating a best-fit line for said plurality of fluorescence intensity ratios $R_F$ and said plurality of pressure values P.

19. The method of claim 18, wherein said best-fit line is calculated using a model selected from the group consisting of: hybrid Voigt, Gaussian or Lorentz distribution.

20. The method of claim 16, wherein said sensor matrix changes in intensity of fluorescence when subjected to tension or compression loading in the range of approximately 0.5 MPa to approximately 110 MPa, and wherein said intensity of fluorescence of the sensor matrix serves as a comparative baseline for an intensity of fluorescence of the plurality of quantum dots.

* * * * *